United States Patent [19]

Chin

[11] Patent Number: 4,559,927
[45] Date of Patent: Dec. 24, 1985

[54] ENDARTERECTOMY APPARATUS AND PROCESS

[75] Inventor: Albert K. Chin, San Francisco, Calif.

[73] Assignee: Thomas J. Fogarty, Palo Alto, Calif.

[21] Appl. No.: 273,920

[22] Filed: Jun. 15, 1981

Related U.S. Application Data

[62] Division of Ser. No. 97,206, Nov. 26, 1979, Pat. No. 4,290,427.

[51] Int. Cl.⁴ .............................................. A61B 17/32
[52] U.S. Cl. ................................. 128/1 R; 128/304; 128/305
[58] Field of Search ..................... 128/304, 305, 1 R

[56] References Cited

U.S. PATENT DOCUMENTS

| | | | |
|---|---|---|---|
| 2,944,552 | 7/1960 | Cannon | 128/304 |
| 3,448,741 | 6/1969 | Dennis et al. | 128/304 |
| 4,030,503 | 6/1977 | Clark | 128/304 |

FOREIGN PATENT DOCUMENTS 584856 12/1977 U.S.S.R. .............................. 128/304

Primary Examiner—Michael H. Thaler
Attorney, Agent, or Firm—Limbach, Limbach & Sutton

[57] ABSTRACT

A center-pull cutting annulus which is radially expansible is employed to achieve complete removal of arteriosclerotic material from occluded arteries.

3 Claims, 9 Drawing Figures

ENDARTERECTOMY APPARATUS AND PROCESS

This application is a division of application Ser. No. 097,206, filed Nov. 26, 1979, now U.S. Pat. No. 4,290,427.

BACKGROUND OF THE INVENTION

The invention relates to an improved means comprising a radially resilient center-pull cutting loop for excising an extended length of arteriosclerotic material from the lumen of an occluded artery.

The present invention constitutes an improvement upon the endarterectomy apparatus shown and described in commonly owned co-pending application, Ser. No. 073,252, filed Sept. 7, 1979 U.S. Pat. No. 4,315,511, which was in turn an improvement upon the basic endarterectomy apparatus shown and described in commonly owned co-pending application, Ser. No. 060,000, filed July 23, 1979, now abandoned.

Other than said co-pending applications and the two U.S. patents identified as prior art in the earlier filed one, I know of no art, prior or otherwise, which is material as to the subject invention.

SUMMARY OF THE INVENTION

In the above-mentioned applications, the use of side-pull cutting loops is taught. The use of such loops is accomplished by threading the side-pulling wire for the loop through a catheter which is emplaced in the artery between the plaque and the undiseased layers of artery. In some cases it is difficult to properly emplace a catheter between the plaque and the undiseased wall of an artery. In some of these instances, however, a catheter may be easily passed through the center of the artery whether the center is either narrowed but patent or totally occluded by soft thrombotic material. The principal object of the invention is to provide an improved endarterectomy cutting loop of the radially expansible type which is adapted to be center-pulled through the artery.

A further object of the invention is to provide an improved process for effecting full removal of an atheroma from an artery.

DESCRIPTION OF THE PREFERRED EMBODIMENT

Figure 1:
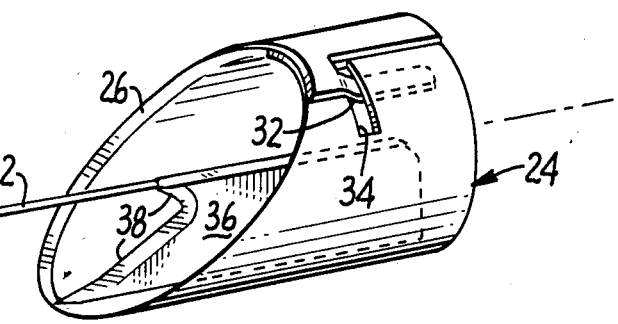
FIG. 1 is an enlarged view in perspective of the center-pull cutting loop of the apparatus of the invention.
Figure 2:
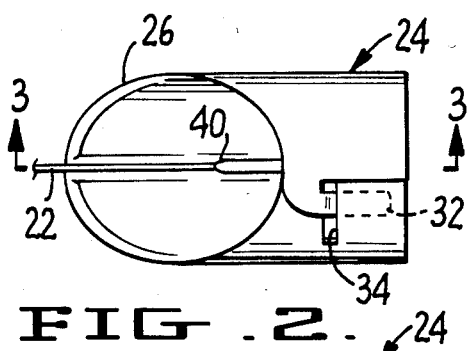
FIG. 2 is a top plan view of the cutting loop of FIG. 1.
Figure 3:
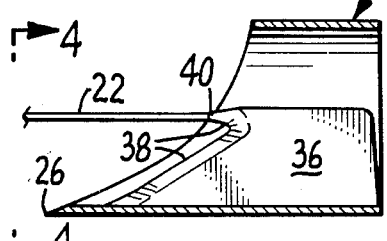
FIG. 3 is a view taken along lines 3—3 of FIG. 2.
Figure 4:
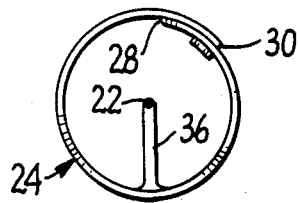
FIG. 4 is a view taken along lines 4—4 of FIG. 3.
Figure 5:
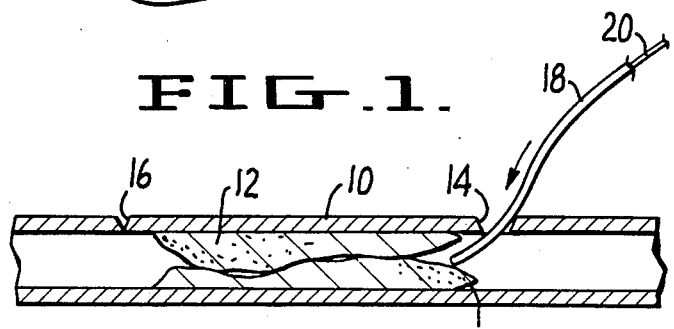
FIG. 5 is a view in diametral section through an occluded artery illustrating the initial stage of emplacement of the apparatus.

In the drawing, the artery 10 contains a section of arteriosclerotic material 12 and is provided with a proximal incision 14 adjacent one end of the material 12 and a distal incision 16 adjacent the other end of the material. Preparatory to the application of the apparatus to the artery 10, an annular plane 17 is cut around the proximal end of the atheroma 12.

Figure 6:
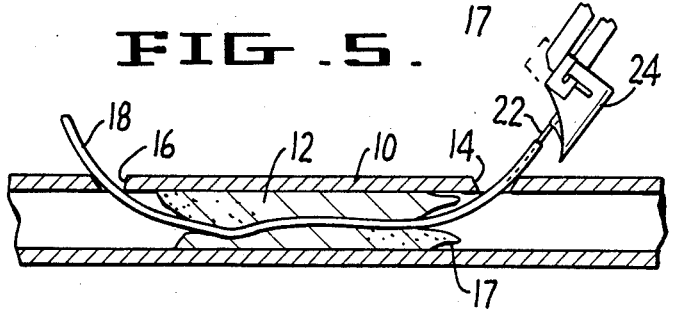
FIG. 6 is a view similar to that of FIG. 5 showing a subsequent stage in emplacement of the apparatus.

The apparatus is conditioned for emplacement by the use of a catheter 18 and a catheter stiffening wire 20, the two being threaded along the central path of least resistance to position the catheter 18 in the position shown in FIG. 6. The stiffening wire 20 is then removed and the loop-pulling wire 22 is threaded through the catheter 18 until the FIG. 7 position is reached.

The annular loop 24 is provided with a cutting edge 26. The loop is longitudinally split along its short side. The resulting ends 28 and 30 are then overlapped. End 30 is provided with an offset tab 32 which extends into a slot 34 formed in the other end 28. This tab and slot connection secures the ends of the loop in overlapped relation to each other while permitting radial compression and expansion of the loop.

The pulling wire 22 is connected to a rib 36 which is attached to the loop along the long side of the loop and extends upwardly therefrom into coincidence with the central longitudinal axis of the loop. The rib is provided with a cutting edge 38 and a forwardly directed tapered extension 40 to which the wire 22 is attached. The cutting edge 26 of the loop slightly precedes the knife edge 38 of rib 36 as the loop is pulled through the artery.

Figure 7:
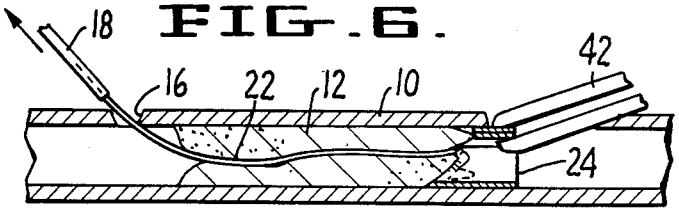
FIG. 7 is a similar view showing the apparatus in the final stage of emplacement.
Figure 8:
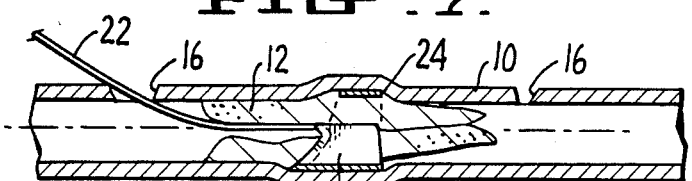
FIG. 8 is a similar view showing the atheroma as being partially excised.
Figure 9:
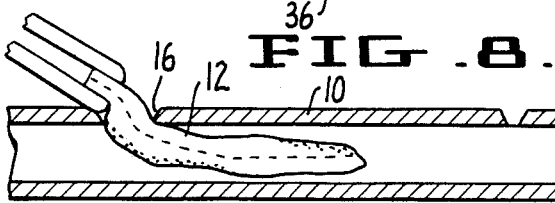
FIG. 9 is a similar view illustrating removal of the detached atheroma from the artery.

Referring again to FIG. 7, the loop 24 is emplaced with its cutting edge disposed in the annular plane 17 and with the loop radially compressed by forceps 42. Before the pulling operation of the loop is commenced, the catheter 18 is removed, as is also indicated in FIG. 7. The loop is then pulled through the plaque by the connecting wire, as shown in FIG. 8. When the atheroma has been fully excised, it is removed from the artery, as shown in FIG. 9.

In the subject endarterectomy process the cutting edge 24 cuts the core of plaque out in annular fashion, while the trailing knife edge 38 of the rib splits the plaque core lengthwise. The excised core is removed in a single piece.

I have discovered that it is important to remove the catheter before the commencement of pulling the cutting loop. The non-cathetered pulling wire 22 tends to cut through the plaque material in the middle of the artery in such a manner as to center the cutting loop with reference to the plaque material as the cutting loop passes through the artery. The cutting wire alone cuts through occlusion irregularities tending to define a tortuous passage for the wire and thus the wire tends to effect a straightline pull along the center axis of the artery as the loop is pulled through the artery. If the catheter 18 were left in place over the pulling wire, the catheter would tend to follow the tortuous passage rather than straightening the passage out by a cutting action, as when the wire is free of the catheter.

The above-mentioned patent applications describe in detail the specifications as to materials which may be suitably used for catheter 18, wires 20 and 22 and loop 24. The wires 20 and 22 are preferably made of stainless spring steel. The loop 24 is preferably made from a section of resilient spring material, such as plastic or stainless steel, suitably connected as by solder or adhesive to wire 22.

CONCLUSION

It is to be understood that the invention is not to be limited to the specifics of the preferred embodiment which has been shown and described, but is instead to be defined only by the appended claims.

What is claimed is:

1. A method for excising arteriosclerotic occlusions from arteries comprising positioning an annular cutting knife within an artery in position to excise an occlusion upon movement of said knife along said artery, said knife being split longitudinally and having overlapped end portions, said knife being radially compressible and expansible while said end portions are overlapped and having a wire carrier fixedly attached thereto along substantially the central axis thereof, and pulling said carrier through a distal incision in said artery.

2. A method for excising arteriosclerotic occlusions from arteries comprising positioning an annular cutting knife within an artery in position to excise an occlusion upon movement of said knife along said artery, said knife being split longitudinally and having overlapped end portions provided with complemental means to maintain said end portions overlapped, said knife being radially compressible and expansible while said end portions are overlapped and having a wire carrier fixedly attached thereto along substantially the central axis thereof, and pulling said carrier through a distal incision in said artery.

3. A method for excising arteriosclerotic occlusions from arteries comprising positioning an annular cutting knife within an artery in position to excise an occlusion upon movement of said knife along said artery, said knife being split longitudinally and having overlapped end portions, said knife being radially compressible and expansible while said end portions are overlapped and having a wire carrier fixedly attached thereto along substantially the central axis thereof, and pulling said carrier through a distal incision in said artery, said wire carrier being emplaced in said occlusion by threading a wire reinforced catheter along the central path of least resistance of said occlusion, removing the wire reinforcement from the catheter, threading said wire carrier through said catheter, removing said catheter, and pulling said carrier through said incision.

* * * * *